US008226973B2

(12) United States Patent
Pan

(10) Patent No.: US 8,226,973 B2
(45) Date of Patent: Jul. 24, 2012

(54) ISOFLAVONE COMPOSITIONS FOR REDUCING ACCUMULATION OF BODY FAT IN MALE MAMMALS, AND METHODS FOR THEIR USE

(75) Inventor: Yuanlong Pan, Chesterfield, MO (US)

(73) Assignee: Nestec, S. A., Vevey (CH)

( * ) Notice: Subject to any disclaimer, the term of this patent is extended or adjusted under 35 U.S.C. 154(b) by 692 days.

(21) Appl. No.: 11/592,471

(22) Filed: Nov. 2, 2006

(65) Prior Publication Data

US 2007/0110789 A1 May 17, 2007

Related U.S. Application Data

(60) Provisional application No. 60/732,737, filed on Nov. 2, 2005.

(51) Int. Cl.
*A61K 31/7048* (2006.01)
*A61K 31/353* (2006.01)
(52) U.S. Cl. ............. 424/442; 514/27; 514/456
(58) Field of Classification Search .......... 514/27, 514/456; 424/442
See application file for complete search history.

(56) References Cited

U.S. PATENT DOCUMENTS

| | | | |
|---|---|---|---|
| 5,554,646 | A | 9/1996 | Cook et al. |
| 5,776,906 | A * | 7/1998 | Sekiya .................. 514/27 |
| 6,204,291 | B1 | 3/2001 | Sunvold et al. |
| 6,335,038 | B1 | 1/2002 | Cavazza |
| 6,359,017 | B1 * | 3/2002 | Bruckner et al. ........... 424/757 |
| RE38,155 | E | 6/2003 | Brown et al. |
| 2001/0000786 | A1 | 5/2001 | Sunvold et al. |
| 2001/0041187 | A1 | 11/2001 | Hastings et al. |
| 2002/0010141 | A1 | 1/2002 | Ingram |
| 2002/0111466 | A1 | 8/2002 | Hendler et al. |
| 2004/0248822 | A1 | 12/2004 | Bruckner et al. |
| 2006/0147607 | A1 | 7/2006 | Beaver et al. |

FOREIGN PATENT DOCUMENTS

| | | |
|---|---|---|
| EP | 0628258 A1 | 12/1994 |
| EP | 1300404 A1 | 4/2003 |
| EP | 0848955 B1 | 7/2003 |
| GB | 2355382 A | 4/2001 |
| JP | 2002/80351 A | 3/2002 |
| WO | WO 97/35491 A1 | 10/1997 |
| WO | WO 01/17374 A1 | 3/2001 |
| WO | WO 03/013268 A1 | 2/2003 |
| WO | WO 03/068218 A1 | 8/2003 |
| WO | WO 2004/014155 A2 | 2/2004 |
| WO | WO 2004/071211 A1 | 8/2004 |
| WO | WO 2004/084885 A1 | 10/2004 |
| WO | WO 2005/058064 A1 | 6/2005 |

OTHER PUBLICATIONS

Bhathena, S.J. and M.T. Velasquez, "Beneficial Role of Dietary Phytoestrogens in Obesity and Diabetes," *Am. J. Clin. Nutr.* vol. 76, pp. 1191-1201, 2002.

Chin, S.F. et al., "Dietary Sources of Conjugated Dienoic Isomers of Linoleic Acid, A Newly Recognized Class of Anticarcinogens," *J. Food Comp. Anal.* vol. 5, pp. 185-197, 1992.
Clarkson, T.B. et al., "Inhibition of Postmenopausal Atherosclerosis Progression: A Comparison of the Effects of Conjugated Equine Estrogens and Soy Phytoestrogens," *J. Clin. Endocrinol. Metab.* vol. 86, pp. 41-47, 2001.
Cooke, P.S. and A. Naaz, "Role of Estrogens in Adipocyte Development and Function," *Exp. Biol. Med.* vol. 229, pp. 1127-1135, 2004.
De Pergola, G.D. "The Adipose Tissue Metabolism: Role of Testosterone and Dehydroepiandrosterone," *Int. J. Obesity*, vol. 24, pp. S59-S63, 2000.
Fang, Y.C. et al., "Effect of Genistein Supplementation on Tissue Genistein and Lipid Peroxidation of Serum, Liver and Low-Density Lipoprotein in Hamster,". *J. Nutr. Biochem.* vol. 15, pp. 142-148, 2004.
Fritz, I.B. and K.T. Yue, "Long-Chain Carnitine Acyltransferase and The Role of Acylcarnitine Derivatives in The Catalytic Increase of Fatty Acid Oxidation Induced by Carnitine," *J. Lipid Res.* vol. 4, pp. 279-288, 1963.
Hand, M.S. et al., "Obesity: Occurrence, Treatment, and Prevention," *Vet. Clin. N. Am. Small Anim. Prac.*, vol. 19, pp. 447-474, 1989.
Harper, E.J. et al.,"Effects of Feeding Regimens on Bodyweight, Composition and Condition Score in Cats Following Ovariohysterectomy," *J. Small Anim. Pract.*, vol. 42, pp. 433-438, 2001.
Kawakami, Y. et al., "Regulative Actions of Dietary Soy Isoflavone on Biological Antioxidative System and Lipid Metabolism in Rats," *J. Agric. Food Chem.* vol. 52, pp. 1764-1768, 2004.
Linford, N.J. and D.M. Dorsa, "17beta-Estradiol and the Phytoestrogen Genistein Attenuate Neuronal Apoptosis Induced by the Endoplasmic Reticulum Calcium-Atpase Inhibitor Thapsigargin," *Steroids*, vol. 67, pp. 1029-1040, 2002.
Lynch, S.M., et al., "Formation of Non-Cyclooxygenasae-Derived Prostanoids (F2-Isoprostanes) in Plasma and Low Density Lipoprotein Exposed to Oxidative Stress in Vitro,"*J. Clin. Invest.* vol. 93, pp. 998-1004, 1994.
Mohamed, M.K. and A.A. Abdel-Rahman, "Effect of Long-Term Ovariectomy and Estrogen Replacement on the Expression of Estrogen Receptor Gene in Female Rats," *Eur. J. Endocrinol.*, vol. 307-314, 2000.
Morrow, J.D. et al., "A Series of Prostaglandin F2-Like Compounds are Produced In Vivo in Humans by a Non-Cyclooxygenase, Free Radical-Catalyzed Mechanism," *Proc. Natl. Acad. Sci. USA*, vol. 87 pp. 9383-9387, 1990.
Naaz, A. et al., "The Soy Isoflavone Genistein Decreases Adipose Deposition in Mice," *Endocrinology*, vol. 144, pp. 3315-3320, 2003.
Robertson, I.D. "The Association of Exercise, Diet and Other Factors with Owner-Perceived Obesity in Privately Owned Dogs from Metropolitan Perth, WA," *Prev. Vet. Med.*, vol. 58, pp. 75-83, 2003.
Sayegh, R.A. et al. "Impact of Hormone Replacement Therapy on the Body Mass and Fat Compositions of Menopausal Women: A Cross-Sectional Study," *Menopause*, vol. 6, pp. 312-315, 1999.
Scarlett J.M. et al., "Overweight Cats: Prevalence and Risk Factors," *Int. J. Obesity*, vol. 18, pp. S22-S28, 1994.

(Continued)

*Primary Examiner* — Shaojia Anna Jiang
*Assistant Examiner* — Ganapathy Krishnan
(74) *Attorney, Agent, or Firm* — Potter Anderson & Corroon LLP; Wendell Ray Guffey, Esq

(57) ABSTRACT

Edible compositions useful for weight management in male animals are disclosed. The compositions comprise one or more isoflavones or isoflavone metabolites and are particularly useful for reducing or preventing the accumulation of body fat. Also disclosed are methods useful for weight management in an animal utilizing compositions comprising one or more isoflavones. The compositions and methods are particularly useful for the reduction or prevention of body fat accumulation during periods of excess caloric intake, and preferably have a sparing effect on lean body mass.

15 Claims, 10 Drawing Sheets

OTHER PUBLICATIONS

Urakawa, H. et al., "Oxidative Stress is Associated with Adiposity and Insulin Resistance in Men," *J. Clin. Endocrinol. Metab.*, vol. 88, pp. 4673-4676, 2003.

Wagner, J.D. et al., "Soy Protein with Isoflavones, but not an Isoflavone-Rich Supplement, Improves Arterial Low-Density Lipoprotein Metabolism and Atherogenesis," *Arterioscler. Thromb. Vasc. Biol.*, vol. 23, pp. 2241,2246, 2003.

Center, S.A., et al., "The clinical and metabolic effects of rapid weight loss in obese pet cats . . . ", J. Vet. Intern. Med., vol. 14, pp. 598-608 (2000) (Abstract).

Cerundolo, R. et al., "Identification and concentration of soy phytoestrogens in commercial dog foods", Am. J. Vet. Res., vol. 65, pp. 592-596 (2004).

Clarkson, T.B., et al., "Inhibition of postmenopausal atherosclerosis progression: a comparison of the effects of . . . ", J. Clin. Endocrinol. Metab., vol. 86, pp. 41-47 (2001).

Court, M.H., et al., "Identification and classification of soy isoflavones in commercial cat foods", Am. J. Vet. Res., vol. 63, pp. 181-185 (2002).

Davi, G., et al., "Lipid peroxidation in diabetes mellitus", Antioxid. Redox. Signal, vol. 7, pp. 256-258 (2005).

Derwent Publications, "Preparation astaxanthin contain powdery composition by drying and pulverize crustacean at . . . ", JP1186346, XP-002342472 (1988) (Abstract).

Jiang, F., et al., "Cardiovascular protective effects of synthetic isoflavone derivatives in apolipoprotein E-deficient mice", J. Vas. Res., vol. 40, pp. 276-284 (2003).

Kandulska, K., et al., "Effect of some phytoestrogens on metabolism of rat adipocytes", Reprod. Nutr. Dev., vol. 39, pp. 497-501 (1999).

Kang, J.O., et al., "Effect of asthaxanthin on the hepatoxicity, lipid peroxidation and antioxidative . . . ", Methods Find. Exp. Clin. Pharmacol., vol. 23, pp. 79-84 (2001).

Merriam-Webster's Collegiate Dictionary, 10th Edition, Merriam-webster, Inc., Springfield Massachusetts, pp. 41 (1996).

Montuschi, P., et al., "Isoprostanes: markers and mediators of oxidative stress", FASEB J., vol. 18, pp. 1791-1800 (2004).

Rahman, S.M., et al., "Effects of conjugated linoleic acid on serum leptin concentration, body-fat accumulation . . . ", Nutrition, vol. 17, pp. 385-390 (2001) (Abstract).

Setchell, K.D.R., et al., "The clinical importance of the metabolite equol-a clue to the effectiveness of soy and its isoflavones", J. Nutr., vol. 132, pp. 3577-3584 (2002).

Stocker, R., at al., "Role of oxidative modification in atherosclerosis", Physiol. Rev., vol. 84, pp. 1381-1478 (2004).

Tzu-Hua, W., et al., "Annual meeting of professional research scientists on experimental biology", New Orleans, LA, Apr. 20-24, 2002, ISSN 0892-6638, Abtract, XP-002342435.

Final Office Action in U.S. Appl. No. 11/082,557, mailed Apr. 7, 2010.

Non-Final Office Action in U.S. Appl. No. 11/082,557, mailed Aug. 28, 2009.

Non-Final Office Action in U.S. Appl. No. 11/082,557, mailed Oct. 5, 2007.

Final Office Action in U.S. Appl. No. 11/082,557, mailed Dec. 15, 2006.

Non-Final Office Action in U.S. Appl. No. 11/082,557, mailed May 22, 2006.

* cited by examiner

ISOFLAVONE COMPOSITIONS FOR REDUCING ACCUMULATION OF BODY FAT IN MALE MAMMALS, AND METHODS FOR THEIR USE

CROSS-REFERENCE TO RELATED APPLICATIONS

This claims benefit of U.S. Provisional Patent Application No. 60/732,737, entitled "Compositions and Methods for Reducing or Preventing Accumulation of Body Fat," filed Nov. 2, 2005.

FIELD OF THE INVENTION

The invention relates to nutrition of companion and other domestic animals. In particular, the invention provides compositions and methods in which isoflavones are used alone or in food, food supplements and the like, to control the accumulation of body fat in subjects, especially male subjects, who consume a normal diet or a caloric excess.

BACKGROUND OF THE INVENTION

Various publications, including patents, published applications, technical articles and scholarly articles are cited throughout the specification. Each of these cited publications is incorporated by reference herein, in its entirety. Full citations for publications not cited fully within the specification are set forth at the end of the specification.

Adipose tissue is a useful energy depot, important for example. for the survival of wild animals because their daily food supply may be limited or uncertain at times. However, the amount of adipose tissue (body fat) in wild animals is much lower than that of domesticated animals. As a result of accumulation of excess adipose tissue, due, for example, to overconsumption of calories and/or lack of exercise, mammals such as humans, or companion animals (e.g. dogs and cats) become overweight or obese.

Animals accumulate fat by eating more calories than are required for energy outputs. If the intake of energy (in the form of calories) exceeds energy expenditure, body fat accumulates. The basal metabolic rate (BMR) is a measure of the energy expended by an animal in a resting state; BMR represents the energy required to perform only normal body functions. If fat is to be removed from the body, fewer calories must be consumed, or more calories must be expended. Physical activity changes the expenditure of energy. Physical inactivity minimizes energy expenditure, yet may contribute to increased food intake. Thus, prolonged or marked decreases in physical activity may lead to obesity.

It has been estimated that in the United States and Europe, 25-44% of domesticated dogs and cats are overweight or obese. (Hand, M S et al. (1989); and, Scarlett, J M et al. (1994)). Animals, such as dogs, that are overweight or obese have health problems, especially in middle age (e.g. dogs that are between about 6-8 years old). If these weight-related health problems remain uncorrected, the risks increase for an animal to develop chronic diseases such as diabetes mellitus, cancer, hypertension, pulmonary, cardiovascular, or degenerative joint disease. In addition, an overweight dog may suffer from skin problems, reduced resistance to infectious diseases, and increased rate of mortality.

Excessive accumulation of body fat occurs when the synthesis of fat exceeds its breakdown. It is known that obesity places increased stress on an animal's body. Increased oxidative stress is believed to be at least partially responsible for the increased risk of the above-mentioned diseases associated with obesity. Substances that inhibit fat synthesis and/or promote fat breakdown may be useful to reduce or prevent excessive accumulation of fat, or obesity in animals, whereas antioxidants may be useful to minimize oxidative damage.

In addition to its role as a storage site for energy surplus, adipose tissue is an endocrine organ. The endocrine system controls a variety of functions in an animal's body through hormones and cytokines. The homeostasis of endocrine hormones, including sex hormones may be disturbed in obese individuals.

Among the sex hormones, estrogens and androgens are now known to play a very important role in energy metabolism, the metabolism and development of adipose tissue, and maintenance of normal body composition. Estrogen, in both male and female animals, plays an important role in regulating the function and development of adipocytes (Cooke, P S et al. (2004)). Thus, menopause in humans and the spaying/neutering of animals are risk factors for obesity development. Indeed, diminished levels of either estrogen or testosterone have been correlated with increased accumulation of body fat. (Pergola, G D (2000); Cookem P S et al. (2004); and, Mohamed, M K et al. (2000)).

The sex hormones may affect adipose tissue in different ways, for example, by affecting the number and size of adipocytes, lipogenesis, and lipolysis, modulating appetite or energy expenditure, and the like. (Pergola G D, 2000; Cooke P S et al., 2004; and, Naaz, A et al., 2003). In this regard, hormone replacement therapy and dietary supplementation have been studied as a means to reverse the effects. (Sayegh R et al., 1999; and, Bhathena S J et al., 2002).

Surgical procedures such as neutering, spaying, ovariectomy, castration, and the like, are frequently performed on animals for population control. However, weight gain is commonly observed in animals following these procedures. (Harper E J et al., 2001; and, Robertson I D, 2003). It is believed that the weight gain is a consequence of the loss of sex hormone production by the sex organs—following the removal of the sex organs there are markedly decreased levels of endogenous sex hormones.

With respect to dietary supplementation, mounting evidence suggests that phytoestrogens may play a role in enhancing lipid metabolism and diminishing deposition of adipose tissue. (Naaz A et al., 2003; Bhathena S J et al., 2002; and Wagner J D et al., 2003). Phytoestrogens are compounds that are produced by plants and have a structure similar to mammalian estrogens (Clarkson T B et al., 2001),. They are capable of interacting with estrogen receptors on adipose tissue in many animal species, including humans, rats, monkeys, and mice. (Naaz A et al., 2003; and, Linford N J et al., 2002). Phytoestrogens are subdivided into three major classifications, coumestans, lignans, and isoflavones. Isoflavones have demonstrated positive effects with respect to reducing adipose deposition, reducing serum low density lipoproteins (LDLs), inhibiting atherosclerosis, and the like, in subjects to which they were administered. (Bhathena S J et al., 2002; Naaz A et al., 2003; Wagner J D et al., 2003; Kawakami Y et al., 2004; and, Fang Y C et al., 2004).

There is thus a need in the art would be to provide compositions and methods that facilitate preserving lean body mass while preventing accumulation of body fat in subjects who are not on a diet regimen or who are consuming more than their minimum caloric requirements.

SUMMARY OF THE INVENTION

In one of its several aspects, the invention provides comestible compositions comprising one or more isoflavones or one or more metabolites thereof, in an amount effective for reducing fat accumulation in a male mammal. Preferably, the mammal has an average daily caloric intake in excess of its minimum daily energy requirement. In one embodiment the mammal is at risk for gaining weight and in particular accumulating excess fat or becoming obese.

In various embodiments, the isoflavones include at least one of daidzein, 6-O-malonyl daidzein, 6-O-acetyl daidzein, genistein, 6-O-malonyl genistein, 6-O-acetyl genistein, glycitein, 6-O-malonyl glycitein, 6-O-acetyl glycitein, biochanin A, or formononetin. The isoflavones or metabolites thereof are from soy bean (Glycine max) in certain embodiments. Where present, the one or more metabolites preferably include equol.

In various embodiments, the comestible composition is a pet food, a human food, or a food supplement—for example to be taken directly, or to be added to a human food, pet food, or to be added to animal feed. Preferred mammals include humans and companion animals, such as dogs or cats, or other animals commonly kept as companions.

In another aspect provided herein, the companion animal has been altered with respect to his sex organs, for example, neutered; has reduced levels of testosterone due to natural causes such a anatomical defect, biochemical or genetic abnormality, or disease, is post-andropausal; has reduced circulating estradiol concentrations relative to a healthy, nonobese control animal of the same species and/or breed; has reduced ability to convert testosterone into estradiol relative to a healthy, nonobese control animal of the same species and/or breed; or has reduced aromatase activity relative to a healthy, nonobese control animal of the same species and/or breed.

In another aspect of the invention, the comestible compositions have a sparing effect on lean body mass.

In yet another aspect of the invention, the comestible composition is provided to a companion animal that is neutered after weaning but before reaching sexual maturity, wherein the comestible composition is fed to the companion animal before the animal reaches a normal adult body weight wherein net weight gain is essential to the companion animal's health or growth. In such embodiments, it is not possible simply to suppress weight gain, rather excess fat accumulation must specifically be reduced or prevented, while lean body must be allowed to increase.

In another of its several aspects, methods are provided for reducing fat accumulation in a male mammal consuming calories in excess of its minimum daily requirement, the methods comprise providing to the mammal on a regular basis a comestible composition comprising one or more isoflavones or metabolites thereof in an amount effective for reducing fat accumulation in the mammal, wherein the mammal has an average daily caloric intake in excess of its minimum daily energy requirement.

As above, the comestible composition preferably comprises one or more of the isoflavones daidzein, 6-O-malonyl daidzein, 6-O-acetyl daidzein, genistein, 6-O-malonyl genistein, 6-O-acetyl genistein, glycitein, 6-O-malonyl glycitein, 6-O-acetyl glycitein, biochanin A, or formononetin.

In one embodiment of the methods provided, the comestible composition is a pet food, a human food, or a food supplement to be taken directly, or to be added to a human food, pet food, or to an animal feed.

Preferably the mammal is a human or a companion animal, for example, a dog or a cat.

In another aspect of the invention, the methods comprise a companion animal that has been surgically- or chemically-altered, for example, neutered; or has reduced testosterone circulating as a result of natural causes such as an anatomical anomaly, or a biochemical or genetic defect, or a disease, is post-andropausal; has reduced circulating estradiol concentrations relative to a healthy, nonobese control animal of the same species and/or breed; has reduced ability to convert testosterone into estradiol relative to a healthy, nonobese control animal of the same species and/or breed; or has reduced aromatase activity relative to a healthy, nonobese control animal of the same species and/or breed.

In another aspect of the invention, methods are employed wherein the composition has a sparing effect on lean body mass.

In one aspect of the invention, preferably the companion animal is neutered after weaning but before reaching sexual maturity, and the comestible composition is provided to the companion animal before the animal reaches a normal adult body weight wherein net weight gain is essential to the companion animal's health or growth.

These and other features and advantages provided herein will be further disclosed by reference to the figures, detailed description, and the examples that follow.

DETAILED DESCRIPTION OF ILLUSTRATIVE EMBODIMENTS

Figure 1:
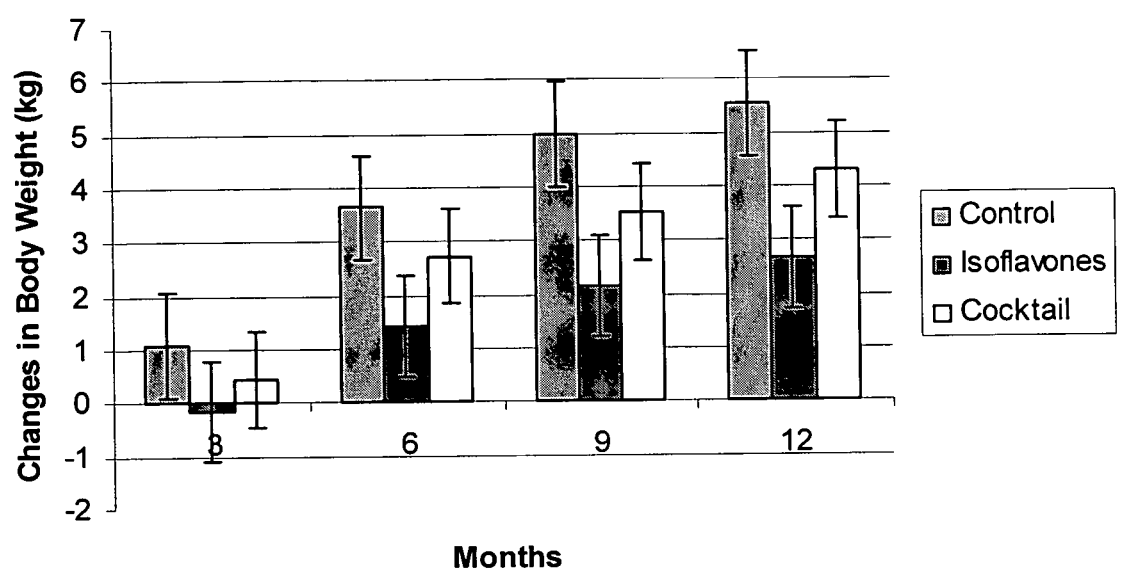
FIG. 1 shows changes in overall body weight over baseline during a 12-month weight management regimen in dogs. All dogs were fed 25% more than their maintenance energy requirement. Dogs were fed a control diet of 29% protein and 18% fat, an isoflavone-containing diet ("isoflavone diet"=control diet supplemented with 10% SGM (soy germ meal)), or a "cocktail diet" (control diet supplemented with 10% SGM, 100 ppm L-carnitine, and 1.5% CLA (conjugated linoleic acid)). Control diet-fed dogs gained significantly more weight than those fed the isoflavone diet ($p=0.043$ at nine months, and $p=0.041$ at twelve months).

Various terms relating to the methods and other aspects of the present invention are used throughout the specification and claims. Such terms are to be given their ordinary meaning in the art unless otherwise indicated. Other specifically defined terms are to be construed in a manner consistent with the definition provided herein.

DEFINITIONS

The following abbreviations may be used in the specification and examples: CLA, conjugated linoleic acid; BCS, body condition score; BMR, basal metabolic rate; MER, maintenance energy requirement; DEXA, dual energy x-ray absorptiometry; BW, body weight; SGM, soy germ meal; and ppm, parts per million.

"Effective amount" refers to an amount of a compound, material, composition, comestible, and/or dosage form as described herein that may be effective to achieve a particular biological result. Such results may include, but are not limited to, reduction and/or prevention of obesity, reduction or prevention of body fat accumulation, and weight management in an animal. Such effective activity may be achieved, for example, by causing or allowing the ingestion of compositions of the present invention. It is to be understood that ingestion here encompasses eating or drinking in any form, and the terms composition, comestible, and food or feed encompass both solid food, liquid food or drink, and any other consumable form such as gels, pastes, emulsions, licks, treats, chews, tablets, pills, or the like.

The present invention relates to any animal, preferably a male and more preferably a male mammal, and still more preferably, male companion animals and humans. A "companion animal" is any domesticated animal, and includes, without limitation, cats, dogs, rabbits, guinea pigs, ferrets, hamsters, mice, gerbils, horses, cows, goats, sheep, donkeys, pigs, and the like. Humans, dogs and cats are presently preferred, and both male and female dogs are exemplified herein in the working examples.

"Male" animals include unaltered and altered male animals of any age. Of particular interest for use herein are "male mammals" of any age that have been altered, for example surgically or chemically, with regard to their sex organs or their ability to produce male hormones. Also useful herein are male animals that as a result of a natural occurrence or an anatomical, biochemical, enzymatic, or genetic defect or anomaly, or disease have altered sex organs or altered ability to produce male hormones. Preferably the mammals have a decreased ability to produce androgenic hormones. As an example, some male animals have anatomically defective testes, for example where the testes fail to properly descend into the scrotum. Such animals may have decreased, absent, or altered male hormones, and may be reproductively "incapable". Also encompassed within the meaning of "male animal" or "male mammal" as used herein are male animals or mammals that for anatomical, biochemical, enzymatic, or genetic reasons, such as defect or anomaly, or as a result of surgery or chemical treatment, or accident or disease, have reduced ability to convert testosterone into estradiol. Other "male" animals include those that have altered or reduced amounts of the aromatase enzyme activity responsible for converting testosterone into estradiol in the normal male animal of the same species and/or breed. In various preferred embodiments, the "male" animals of the invention are neutered; or post-andropausal; or have reduced circulating estradiol concentrations relative to a healthy, nonobese control animal of the same species and/or breed; or have reduced ability to convert testosterone into estradiol relative to a healthy, nonobese control animal of the same species and/or breed; or have reduced aromatase activity relative to a healthy, nonobese control animal of the same species and/or breed, or a combination of the foregoing. It is sometimes useful to compare a "male" to an equivalent aged animal of the same species and/or breed. IN other cases it may be preferred to compare for example a young neutered animal to a healthy adult, or a aged or older animal to a healthy younger adult. Such comparisons where useful are contemplated herein.

"Obesity" refers to an increase in body weight beyond the limitation of skeletal and physical requirement, as the result of an excessive accumulation of fat in the body. As used herein, "fat accumulation" encompasses any biological means of lipid deposition that can alter body composition in a measurable way over time. Most preferably, fat accumulation refers to the deposit of excess subcutaneous fat and intramuscular fat, and not for example to alteration of the internal fat, such as the fat surrounding certain vital organs. A reduction of fat accumulation is preferably measurable by a macroscopic determination of gross body composition—e.g. a determination of body fat can be determined by a variety of means known to those of skill in the art such as but not limited to skin calipers, electrical impedance, or underwater weighing operations in live animals. Physical measurement of body fat and lean body mass is possible in post-mortem animals by a variety of means that are precluded for living animals. Lean body mass in live animals can be calculated by means known to those of skill of often involves simple calculations based on body fat measurements, such as determination by difference. A "nonobese" animal is one whose body weight is within the accepted norms for an animal of that species and/or breed having similar skeletal and physical composition/size/frame, and who does not have an excessive accumulation of fat in or on its body. The animal need not be at a particular "ideal weight" to be nonobese, however as indicated below a measure such as BCS may be useful to determine a range of useful body weights. As used herein, nonobese animals are preferably not substantially underweight according to a scale such as the BCS below (e.g. less than about 2 on the BCS scale).

"Overweight" refers to weighing more than is normal or necessary, especially having more body weight than is considered normal or healthy for one's age or build. Overweight or obesity may sometimes be referred to herein as a numerical "score", using a body conditioning scoring system in which a BCS (body condition score) of 1-3 indicates too thin or underweight, BCS of 4-5 indicates ideal condition or weight, and BCS of 6-9 indicates overweight to obese.

As used herein, the term "pet food" or "pet food composition" means a composition that is intended for ingestion by an animal, and preferably by companion animals. A "complete and nutritionally balanced pet food," is one that contains all known required nutrients in appropriate amounts and proportions based on recommendations of recognized authorities in the field of companion animal nutrition, and is therefore capable of serving as a sole source of dietary intake to maintain life or promote production, without the addition of supplemental nutritional sources. Nutritionally balanced pet food compositions are widely known and widely used in the art.

As used herein, a "dietary supplement" or "food supplement" is a product that is intended to be ingested in addition to the normal diet of an animal, or added to a food or feed, or added to a fluid intended for consumption by the animal.

As used herein, a "food product formulated for human consumption" is any composition intended for ingestion by a human being.

A "weight control program" refers to a regimen designed to prevent and/or reduce obesity in an animal. Such a regimen may include, without limitation, the use of a particular pet food, pet food composition, dietary supplement, or food product formulated for human consumption, alone or in or any suitable combination.

"Weight management" refers to the promotion of healthy weight maintenance in an animal (including a human), whether or not the animal is on a formalized weight control program. The term encompasses the reduction or prevention of accumulation of body fat and/or the preservation of lean body mass when the animal is consuming a normal diet or a caloric excess. Weight management may also entail allowing for adequate weight gain. For example, it is common for very young animals to be neutered or spayed as part of population control measures. The proper weight management for such young animals may seek to avoid unnecessary or undesirable fat accumulation while permitting or enabling adequate weight gain (e.g. lean body mass) for sound health of the young animal and proper maturation into adulthood. Reducing fat accumulation, and thus a significant step in weight management may be accomplished by, among other things, enhancing fat or adipose tissue catabolism, an enhancing fatty acid oxidation, and/or diminishing fat or adipose tissue anabolism. Increasing lean body mass may also increase the caloric requirement for basic maintenance and thus lead to a decrease in fat accumulation or even a net loss of fat.

"Adipose tissue" refers to the connective tissue comprising fat cells (also referred to as adipocytes) and their surrounding reticular fibers and reticular network. Adipose tissue is generally where the body deposits and stores excess fat. Adipose tissue encompasses, without limitation, white, brown, and yellow adipose tissue.

"Catabolism" refers to the metabolic breakdown of complex molecules into simpler molecules. With respect to the catabolism of adipose tissue, the term encompasses the metabolic breakdown of fat stores into energy and/or a reduction in the number or size of adipocytes.

"Anabolism" refers to the metabolic processes in which simple substances are synthesized into the complex materials. With respect to anabolism of adipose tissue, the term encompasses the formation of triglycerides, genesis of adipocytes, the generation of the adipose reticular network, and the like.

As used herein, "isoflavones" refers to 3-phenylchromones, isomeric forms of flavones in which the benzene group is attached to the 3 position of the benzopyran ring instead of the 2 position, and their respective metabolites. Whenever the term "isoflavones" is used herein, it is intended to encompass derivatives and metabolites of isoflavones, with particular examples of isoflavone derivatives as described herein. Isoflavones may be found in a number of sources, including, but not limited to, soy. Non-limiting examples of isoflavones include daidzein, 6-O-malonyl daidzein, 6-O-acetyl daidzein, genistein, 6-O-malonyl genistein, 6-O-acetyl genistein, glycitein, 6-O-malonyl glycitein, 6-O-acetyl glycitein, biochanin A, formononetin, or any metabolites of isoflavones. Isoflavones and certain benefits to health derived from their use have been described in the scientific literature (see, e.g., Setchell K D R, Adlercreutz H. Mammalian lignans and phytoestrogens. Recent studies on their formation, metabolism and biological role in health and disease. In: Rowland I A, ed. The Role of Gut Microflora in Toxicity and Cancer. New York: Academic Press 1988: 315-345). For instance, soy has been found to reduce the risk of cardiovascular disease; reduce the risk of breast and prostate cancer; relieve hot flushes associated with menopausal estrogen deficiency; retard osteoporosis in postmenopausal women; reduce total amount of cholesterol, LDL cholesterol, and triglycerides in plasma; preserve cognitive functions in postmenopausal women; improve symptoms of hypertension and promote weight loss.

"Carnitine" refers to a trimethylammonium (betaine) derivative of γ-amino-β-hydroxybutyric acid, formed from $N_8,N_8,N_8$-trimethyllysine and from γ-butyrobetaine. L-carnitine is an acyl carrier with respect to the mitochondrial membrane; it thus stimulates fatty acid oxidation. It is sometimes referred to as Vitamin Bt or Vitamin B7 (Fritz I B et al. 1963).

"Conjugated linoleic" or "CLA" is a collective term used to designate a mixture of positional and geometric isomers of the essential (n-6) fatty acid linoleic acid (Chin S F et al. 1992).

"Neutered," refers to the animal lacking or having imperfectly developed or nonfunctional generative organs, whether such condition occurs congenitally, by natural development processes, or through intervening surgery.

"Castrate" refers to the removal of the testicles of a male animal.

"Spay" refers to the removal of the ovaries of a female animal.

Description:

It has been discovered in accordance with the present invention that isoflavones and various metabolites thereof are effective for the prevention or reduction of body fat accumulation during periods of caloric excess, that is, when a subject is routinely consuming more food than needed to meet minimum energy requirements. This effect is particularly pronounced in males. It is believed that the effectiveness of isoflavones in this aspect of weight management heretofore has not been appreciated.

Accordingly, one aspect of the invention features compositions comprising one or more isoflavones or metabolites thereof in an amount effective for weight management in animals, and more preferably in an amount effective to reduce or prevent fat accumulation specifically. In certain embodiments, the animals are companion animals such as dogs or cats. In another embodiment, the animal is a human. In certain embodiments, the animal is post-menopausal (estrogen deficiency) or post-andropausal (androgen and estrogen deficiency), or neutered (androgen and estrogen deficiency). In preferred embodiments, the animal is male, preferably a mammal.

Thus in one aspect, the invention provides comestible compositions comprising one or more isoflavones or metabolites thereof, in an amount effective for reducing fat accumulation in a male mammal, wherein the mammal has an average daily caloric intake in excess of its minimum daily energy requirement. In one embodiment, the isoflavones include at least one of daidzein, 6-O-malonyl daidzein, 6-O-acetyl daidzein, genistein, 6-O-malonyl genistein, 6-O-acetyl genistein, glycitein, 6-O-malonyl glycitein, 6-O-acetyl glycitein, biochanin A, or formononetin. Preferably the isoflavones or metabolites thereof are from soy bean. In one embodiment, the metabolites in the comestible include equol.

The comestible composition in various embodiments is a pet food, a human food, or a food supplement to be taken directly or added to a human food, pet food, or to animal feed.

In various embodiments, the mammal is a human or a companion animal, e.g. a dog or a cat. In other embodiments, the companion animal has been neutered; is post-andropausal; has reduced circulating estradiol concentrations relative to a healthy, nonobese control animal of the same species and/or breed; has reduced ability to convert testosterone into estradiol relative to a healthy, nonobese control animal of the same species and/or breed; or has reduced aromatase activity relative to a healthy, nonobese control animal of the same species and/or breed. In other embodiments the testosterone levels of the animal are deficient for reason relating to genetic or biochemical anomalies, or due the age or health status (e.g. a disease) of the animal.

The comestible compositions preferably have a sparing effect on lean body mass.

In another aspect of the invention, the comestible composition is used wherein the companion animal is neutered after weaning but before reaching sexual maturity. The comestible composition is fed to the companion animal before the animal reaches a normal adult body weight wherein net weight gain is essential to the companion animal's health or growth. This is often the requirements of animals that surgically altered at a young age—a procedure which is frequently part of a population control effort.

The isoflavones or metabolites thereof can be present in the composition as an ingredient or additive. In one preferred embodiment, the isoflavones are soy isoflavones. In a more preferred embodiment, the isoflavones are daidzein, 6-O-malonyl daidzein, 6-O-acetyl daidzein, genistein, 6-O-malonyl genistein, 6-O-acetyl genistein, glycitein, 6-O-malonyl glycitein, 6-O-acetyl glycitein, biochanin A, or formononetin, or metabolites thereof. In one preferred embodiment, the isoflavones metabolite is dihydrodaidzein or equol. In a preferred embodiment, the compositions of the invention are food compositions for humans or companion animals, such as dogs and cats. In certain embodiments, the foods are pet foods. These include foods intended to supply necessary dietary requirements, as well as treats (e.g., biscuits), chews, or other dietary supplements. Optionally, the pet food compositions can be a dry composition (for example, kibble), semi-moist composition, wet composition, or any mixture thereof. In another preferred embodiment, the composition comprises a dietary supplement, such as a gravy, drinking water, beverage, yogurt, powder, granule, paste, suspension, chew, morsel, treat, snack, pellet, pill, capsule, tablet, or any other delivery form. In a detailed embodiment, the dietary supplement can comprise a high concentration of isoflavones or metabolites thereof such that the supplement can be administered to the animal in small amounts, or in the alternative, can be diluted before administration to an animal. The dietary supplement may require admixing with water prior to administration to the animal.

The composition may be refrigerated or frozen. The isoflavones or metabolites thereof may be pre-blended with the other components of the composition to provide the beneficial amounts needed, may be coated onto a pet food composition, or may be added to the composition prior to offering it to the animal, for example, using a sprinkled powder or a mix.

The compositions of the invention comprise isoflavones or metabolites thereof in an amount effective for weight management in an animal to which the composition has been administered. For pet foods, the amount of isoflavones or metabolites thereof as a percentage of the composition is in the range of about 0.1% to about 30% in certain embodiments, up to 50% in other embodiments, and about 10.0% in specific embodiments, of the composition on a dry matter basis, although a greater percentage can be supplied. In various embodiments, the amount is about 1.0%, 1.5%, 2.0%, 2.5%, 3.0%, 3.5%, 4.0%, 4.5%, 5.0%, 5.5%, 6.0%, 6.5%, 7.0%, 7.5%, 8.0%, 8.5%, 9.0%, 9.5%, 10.0%, 10.5%, 11.0%, 11.5%, 12.0%, 12.5%, 13.0%, 13.5%, 14.0%, 14.5%, 15.0%, 15.5%, 16.0%, 16.5%, 17.0%, 17.5%, 18.0%, 18.5%, 19.0%, 19.5%, 20.0%, 20.5%, 21.0%, 21.5%, 22.0%, 22.5%, 23.0%, 23.5%, 24.0%, 24.5%, 25.0%, 25.5%, 26.0%, 26.5%, 27.0%, 27.5%, 28.0%, 28.5%, 29.0%, 29.5%, 30%, or more of the composition on a dry matter basis. Dietary supplements may be formulated to contain several-fold higher concentrations of isoflavones or metabolites thereof, to be amenable for administration to an animal in the form of a tablet, capsule, liquid concentrated, or other similar dosage form, or to be diluted before administrations, such as by dilution in water, spraying or sprinkling onto a pet food, and other similar modes of administration.

The sources of each of the isoflavones or metabolites thereof can be any suitable source, synthetic or natural. Preferred sources of isoflavones include any isoflavones-containing plant, plant material, or plant extract, such as, but not limited to, legumes, clovers, and kudzu root. Preferred legume sources of isoflavones include chick peas, lentils, soy beans, or any other type of beans or peas that contain isoflavones. Soybean meal, soygerm meal, and the like may also be used. Preferred clover sources of isoflavones include red clover and subterranean clover. Alternatively, the isoflavones or metabolites thereof may be synthesized de novo according to any means suitable in the art.

The compositions of the invention can optionally comprise supplementary substances such as minerals, vitamins, salts, condiments, colorants, and preservatives. Non-limiting examples of supplementary minerals include calcium, phosphorous, potassium, sodium, iron, chloride, boron, copper, zinc, manganese, iodine, selenium and the like. Non-limiting examples of supplementary vitamins include vitamin A, various B vitamins, vitamin C, vitamin D, vitamin E, and vitamin K. Additional dietary supplements may also be included, for example, niacin, pantothenic acid, inulin, folic acid, biotin, amino acids, and the like.

The compositions of the invention can optionally comprise one or more supplementary substances that promote or sustain general weight management, or aid in the reduction or prevention of fat accumulation. Such substances include, without limitation, chitosan, chromium picolinate, psyllium, glucomannan, guar gum, hydroxy-methylbutyrate, pyruvate, and extracts from *Ephedra sinica, Garcinia cambogia, Ilex paraguariensis, Paullinia cupana,* and *Pausinystalia yohimbe.*

In various embodiments, pet food or pet treat compositions of the invention can comprise, on a dry matter basis, from about 15% to about 50% crude protein, by weight of the composition. The crude protein material may comprise vegetable proteins such as soybean, cottonseed, and peanut, or animal proteins such as casein, albumin, and meat protein. Non-limiting examples of meat protein useful herein include pork, lamb, equine, poultry, fish, and mixtures thereof.

The compositions may further comprise, on a dry matter basis, from about 5% to about 40% fat, by weight of the composition. The compositions may further comprise a source of carbohydrate. The compositions may comprise, on a dry matter basis, from about 15% to about 60% carbohydrate, by weight of the composition. Non-limiting examples of such carbohydrates include grains or cereals such as rice, corn, milo, sorghum, alfalfa, barley, soybeans, canola, oats, wheat, and mixtures thereof. The compositions may also optionally comprise other materials such as dried whey and other dairy by-products.

The compositions may also comprise at least one fiber source. A variety of soluble or insoluble fibers may be utilized, as will be known to those of ordinary skill in the art. The fiber source can be beet pulp (from sugar beet), gum arabic, gum talha, psyllium, rice bran, carob bean gum, citrus pulp, pectin, fructooligosaccharide additional to the short chain oligofructose, mannanoligofructose, soy fiber, arabinogalactan, galactooligosaccharide, arabinoxylan, or mixtures thereof. Alternatively, the fiber source can be a fermentable fiber. Fermentable fiber has previously been described to provide a benefit to the immune system of a companion animal. Fermentable fiber or other compositions known to those of skill in the art which provide a prebiotic composition to enhance the growth of probiotic microorganisms within the intestine may also be incorporated into the composition to aid in the enhancement of the benefit provided by the present invention to the immune system of an animal. Additionally, probiotic microorganisms, such as *Lactobacillus* or *Bifidobacterium* species, for example, may be added to the composition.

In one embodiment, the composition is a complete and nutritionally balanced pet food. In this context, the pet food may be a wet food, a dry food, or a food of intermediate moisture content, as would be recognized by those skilled in the art of pet food formulation and manufacturing. "Wet food" describes pet food that is typically sold in cans or foil bags, and has a moisture content typically in the range of about 70% to about 90%. "Dry food" describes pet food which is of a similar composition to wet food, but contains limited moisture content, typically in the range of about 5% to about 15%, and therefore is presented, for example, as small biscuit-like kibbles. The compositions and dietary supplements may be specially formulated for adult animals, or for older or young animals, for example, a "puppy," formulation "kitten" formulation, or a "senior" formulation. In general, specialized formulations will comprise energy and nutritional requirements appropriate for animals at different stages of development or age.

Certain aspects of the invention are preferably used in combination with a complete and balanced food (for example, as described in National Research Council, 1985, Nutritional Requirements for Dogs, National Academy Press, Washington D.C., or Association of American Feed Control Officials, Official Publication 1996). That is, compositions comprising isoflavones or metabolites thereof according to certain aspects of this invention are preferably used with a high-quality commercial food. As used herein, "high-quality commercial food" refers to a diet manufactured to produce the digestibility of the key nutrients of 80% or more, as set forth in, for example, the recommendations of the National Research Council above for dogs, or in the guidelines set forth by the Association of American Feed Control Officials. Similar high nutrient standards would be used for other animals.

The skilled artisan will understand how to determine the appropriate amount of isoflavones or metabolites thereof to be added to a given composition. Such factors that may be taken into account include the type of composition (e.g., pet food composition versus dietary supplement), the average consumption of specific types of compositions by different animals, and the manufacturing conditions under which the composition is prepared. Preferably, the concentrations of isoflavones or metabolites thereof to be added to the composition are calculated on the basis of the energy and nutrient requirements of the animal. According to certain aspects of the invention, the isoflavones or metabolites thereof can be added at any time during the manufacture and/or processing of the composition. This includes, without limitation, as part of the formulation of the pet food composition or dietary supplement, or as a coating applied to the pet food composition or dietary supplement.

The compositions can be made according to any method suitable in the art such as, for example, that described in Waltham Book of Dog and Cat Nutrition, Ed. A T B Edney, Chapter by A. Rainbird, entitled "A Balanced Diet" in pages 57 to 74, Pergamon Press Oxford.

Methods:

Another aspect of the invention features methods for weight management, particularly reduction or prevention of fat accumulation, in an animal, comprising administering to the animal a composition comprising one or more isoflavones or metabolites thereof in an amount effective for weight management in the animal.

Thus in one of its aspects, the invention provides methods for reducing fat accumulation in a male mammal consuming calories in excess of its minimum daily requirement. The methods comprise providing to the mammal on a regular basis a comestible composition comprising one or more isoflavones or metabolites thereof in an amount effective for reducing fat accumulation in the mammal, wherein the mammal has an average daily caloric intake in excess of its minimum daily energy requirement.

In one embodiment, the methods comprise comestible composition having one or more of the isoflavones daidzein, 6-O-malonyl daidzein, 6-O-acetyl daidzein, genistein, 6-O-malonyl genistein, 6-O-acetyl genistein, glycitein, 6-O-malonyl glycitein, 6-O-acetyl glycitein, biochanin A, or formononetin. Preferably, the isoflavones or metabolites thereof are from soy bean.

In one embodiment, one or more metabolites include equol.

Preferably, the comestible composition is a pet food, a human food, or a food or dietary supplement to be taken directly or added to a human food, pet food, or to animal feed. In presently preferred embodiments, the mammal is a human or a companion animal, for example, a dog or a cat.

In another aspect of the methods provided herein the companion animal has been neutered; is post-andropausal; has reduced circulating estradiol concentrations relative to a healthy, nonobese control animal of the same species and/or breed; has reduced ability to convert testosterone into estradiol relative to a healthy, nonobese control animal of the same species and/or breed; or has reduced aromatase activity relative to a healthy, nonobese control animal of the same species and/or breed.

Preferably as used in the method provided herein, the compositions have a sparing effect on lean body mass.

In another aspect of the invention, the companion animal is neutered after weaning but before reaching sexual maturity. The comestible composition is provided to the companion animal before the animal reaches a normal adult body weight wherein net weight gain is essential to the companion animal's health or growth.

In one embodiment of the methods, the composition is provided by administering to the animal on a daily basis, or more frequently than daily basis. In another embodiment, the administration is less than daily, for example one, two, three, or four times weekly, or every second or third or even fourth day. Preferably, the composition is administered to the animal as part of a dietary regimen. In certain embodiments, for example for research purposes or for commercial applications hereof, the amount of the composition actually consumed is monitored.

In another embodiment, the male mammal receiving the comestible is beyond the mid-point of the life expectancy for its species and/or breed. In another, the mammal is a neutered puppy or kitten, preferably post-weaning by at least several weeks.

In one embodiment, the circulating estradiol of the animal is less than about 80% of a healthy, nonobese control animal of the same species and/or breed. In others, the circulating estradiol of the animal is less than about 70, 60, or even 50% of a healthy, nonobese control animal of the same species and/or breed. In still others it is less than about 40, 30 or 20% of a healthy, nonobese control animal of the same species and/or breed. In yet other embodiments, the circulating estradiol of the animal is less than about 15, 10 or 5% of a healthy, nonobese control animal of the same species and/or breed. In one embodiment there is less than 5, 4, 3, 2 or 1% of that of the control animal.

In one embodiment, the composition is a pet food composition or a dietary supplement, as exemplified herein. In a further detailed embodiment, the isoflavones are daidzein, 6-O-malonyl daidzein, 6-O-acetyl daidzein, genistein, 6-O-malonyl genistein, 6-O-acetyl genistein, glycitein, 6-O-malonyl glycitein, 6-O-acetyl glycitein, biochanin A, or formononetin, or metabolites thereof. In another detailed embodiment, the isoflavones metabolite is dihydrodaidzein or equol. In certain embodiments, the animal is a companion animal such as a dog or cat. In one embodiment, the animal is a dog. In another embodiment, the animal is a human. In certain embodiments, the animal is post-menopausal (deficient in estrogen) or post-andropausal (deficient in estrogen and androgen). In preferred embodiments, the animal is male.

The compositions can be administered to the animal by any of a variety of alternative routes of administration. Such routes include, without limitation, oral, intranasal, intravenous, intramuscular, intragastric, transpyloric, subcutaneous, rectal, and the like. Preferably, the compositions are administered orally. As used herein, the term "oral administration" or "orally administering" means that the animal ingests or a human is directed to feed, or does feed, the animal one or more of the inventive compositions described herein.

Wherein the human is directed to feed the composition, such direction may be that which instructs and/or informs the human that use of the composition may and/or will provide the referenced benefit, for example, the enhancement of cognitive function in the animal. Such direction may be oral direction (e.g., through oral instruction from, for example, a physician, veterinarian, or other health professional, or radio or television media (i.e., advertisement), or written direction (e.g., through written direction from, for example, a physician, veterinarian, or other health professional (e.g., prescriptions), sales professional or organization (e.g., through, for example, marketing brochures, pamphlets, or other instructive paraphernalia), written media (e.g., internet, electronic mail, or other computer-related media), and/or packaging associated with the composition (e.g., a label present on a container holding the composition).

Administration can be on an as-needed or as-desired basis, for example, once-monthly, once-weekly, daily, or more than once daily. Similarly, administration can be every other day, week, or month, every third day, week, or month, every fourth day, week, or month, and the like. Administration can be multiple times per day. When utilized as a supplement to ordinary dietetic requirements, the composition may be administered directly to the animal or otherwise contacted with or admixed with daily feed or food. When utilized as a daily feed or food, administration will be well known to those of ordinary skill.

Administration can also be carried out as part of a diet regimen in the animal. For example, a diet regimen may comprise causing the regular ingestion by the animal of a composition comprising one or more isoflavones or metabolites thereof, in an amount effective for weight management in the animal. Regular ingestion can be once a day, or two, three, four, or more times per day, on a daily basis. The goal of regular ingestion is to provide the animal with the preferred daily dose of isoflavones or metabolites thereof, as exemplified herein.

Preferred daily does ranges for isoflavones and/or metabolites thereof ranges from about 5 mg/day to about 5000 mg/day per animal. Preferably, the daily dose of isoflavones and/or metabolites thereof ranges from about 30 mg/day to about 500 mg/day per animal, and more preferably from about 80 mg/day to about 300 mg/day per animal. The daily dose of isoflavones or metabolites thereof can be measured in terms of grams of isoflavones or metabolites thereof per kg of body weight (BW) of the animal. The daily dose of isoflavones or metabolites thereof can range from about 0.001 g/kg to about 50 g/kg BW of the animal, although greater or lesser doses can be provided. Preferably, the daily dose of isoflavones or metabolites thereof is from about 0.001 g/kg to about 25 g/kg BW of the animal. More preferably, the daily dose of isoflavones or metabolites thereof is from about 0.001 g/kg to about 10 g/kg BW of the animal. More preferably, the daily dose of isoflavones or metabolites thereof is from about 0.001 g/kg to about 5 g/kg BW of the animal. More preferably, the daily dose of isoflavones or metabolites thereof is from about 0.001 g/kg to about 1 g/kg BW of the animal. More preferably, the daily dose of the isoflavones or metabolites thereof is from about 0.001 g/kg to about 0.15 g/kg BW of the animal.

According to the methods of the invention, administration of the isoflavones or metabolites thereof, including administration as part of a diet regimen, can span a period of time ranging from parturition through the adult life of the animal.

The following examples are provided to describe the invention in greater detail. They are intended to illustrate, not to limit, the invention.

Example 1

Effect of Dietary Soy Isoflavones on Body Fat in Normal Dogs

Dogs and Diets

Forty two normal, non-obese Labrador Retrievers (Male: <17.5% Body Fat; Female <20% Body Fat) were used in the study. Dogs were randomized into three groups: Group 1 consisted of 13 Labrador Retrievers, which were fed the control diet comprising 29% protein and 18% fat. Group 2 consisted of 14 Labrador Retrievers, which were fed the control diet supplemented with 10% soy germ meal (SGM). Group 3 consisted of 15 Labrador Retrievers, which were fed the control diet supplemented with 10% SGM, 100 ppm L-carnitine, and 1.5% CLA. SGM contains the following soy isoflavones: 17% genistein, 52% daidzein, and 31% glycitein.

All dogs were given a pre-study MER determination. Before the study, and every three months after the study began, the following measurements were made for each animal: body weight, body condition score (BCS), DEXA, blood leptin, thyroid profile, intravenous glucose tolerance test, and determination of blood plasma concentrations of isoflavones and isoflavones metabolites.

Each group of dogs were fed 125% of their basal MER. The duration of the study was twelve months.

General Weight Management Results:

Results are shown in FIGS. 1-4. Weight gain in normal dogs was significantly lower in the isoflavones group than in the control group after 9 (p=0.043, Control vs. Isoflavone group), and 12 months (p=0.041, Control vs. Isoflavone group) of feeding. Throughout the 12-month study, the average weight gain in the control dogs was twice as much as that of the isoflavone-fed dogs (FIG. 1).

Figure 2:
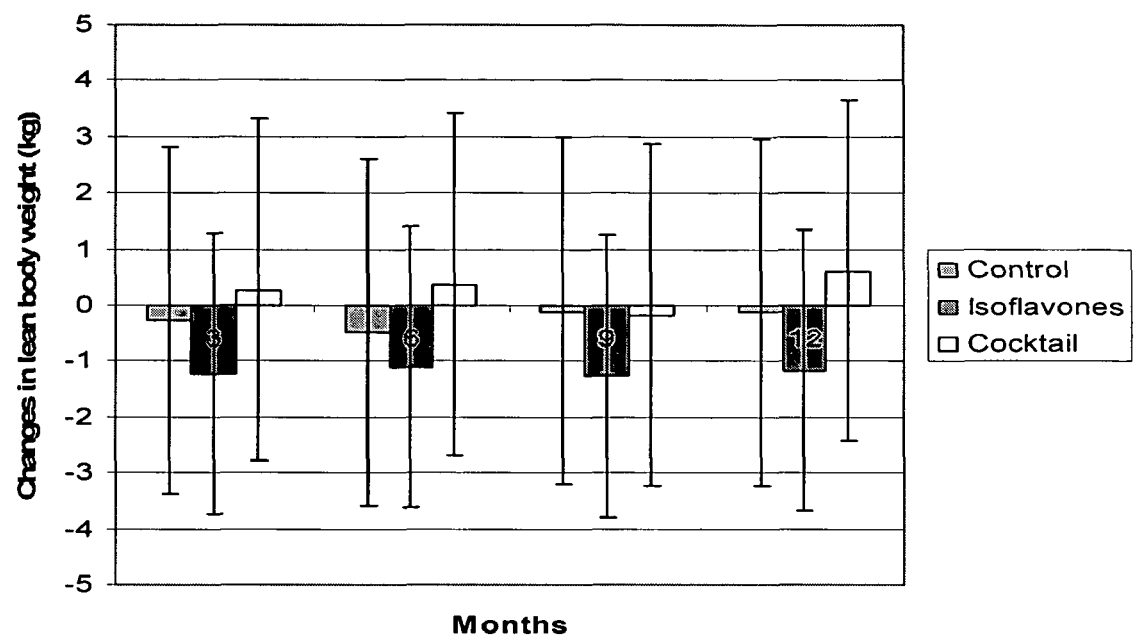
FIG. 2 shows changes in lean body weight over baseline during the 12 month weight management regimen in the dogs fed either the control diet, the isoflavone diet, or the cocktail diet. All dogs were fed 25% excess over their maintenance energy requirement (i.e., 125% of MER). There was no significant difference in lean body mass among the three groups of dogs over the 12 month feeding study, indicating that the significantly higher weight gain in the control dogs was due to higher body fat accumulation.

There was no difference in lean body mass changes among the three groups of dogs over the 12-month of feeding study, indicating that the significantly higher weight gain in the control dogs was due to higher body fat accumulation in normal dogs (FIG. 2).

Figure 3:
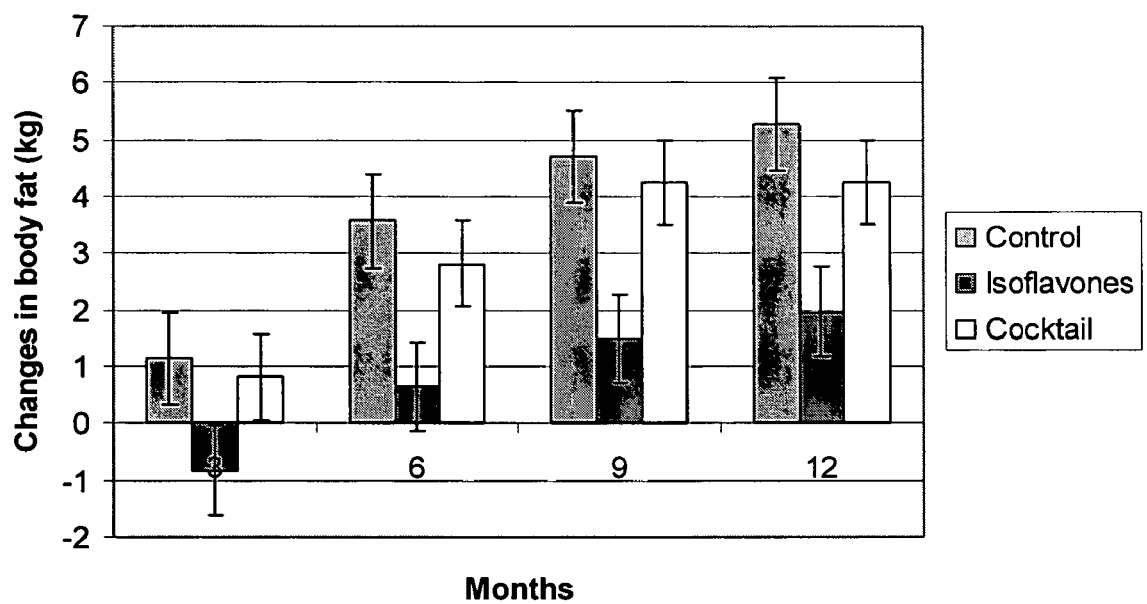
FIG. 3 shows changes in the amount of body fat over baseline during the 12 month weight management regimen in the dogs fed either the control diet, the isoflavone diet, or the cocktail diet. As above, all dogs were fed 25% more than their maintenance energy requirement. Dogs fed the isoflavone diet gained significantly less body fat relative to both the control diet-fed and cocktail diet-fed dogs, as measured at 3, 6, 9, and 12 months ($p<0.05$).

Both control and cocktail groups gained significantly more body fat than the isoflavone group. Control dogs had 5-, 3-, and 2.7-times more average body fat gain than the isoflavone-fed dogs after 6 (p=0.013, Control vs. Isoflavone group), 9 (p=0.007, Control vs. Isoflavone group) and 12 months (p=0.006, Control vs. Isoflavone group) of feeding, respectively. The cocktail-fed dogs had 4.4, 2.8, and 2.2 times more average body fat gain than the isoflavone-fed dogs after 6 (p=0.05, Cocktail vs. Isoflavone group), 9 (p=0.014, Cocktail vs. Isoflavone group) and 12 (p=0.041, Cocktail vs. Isoflavone group) months of feeding, respectively (FIG. 3).

Figure 4:
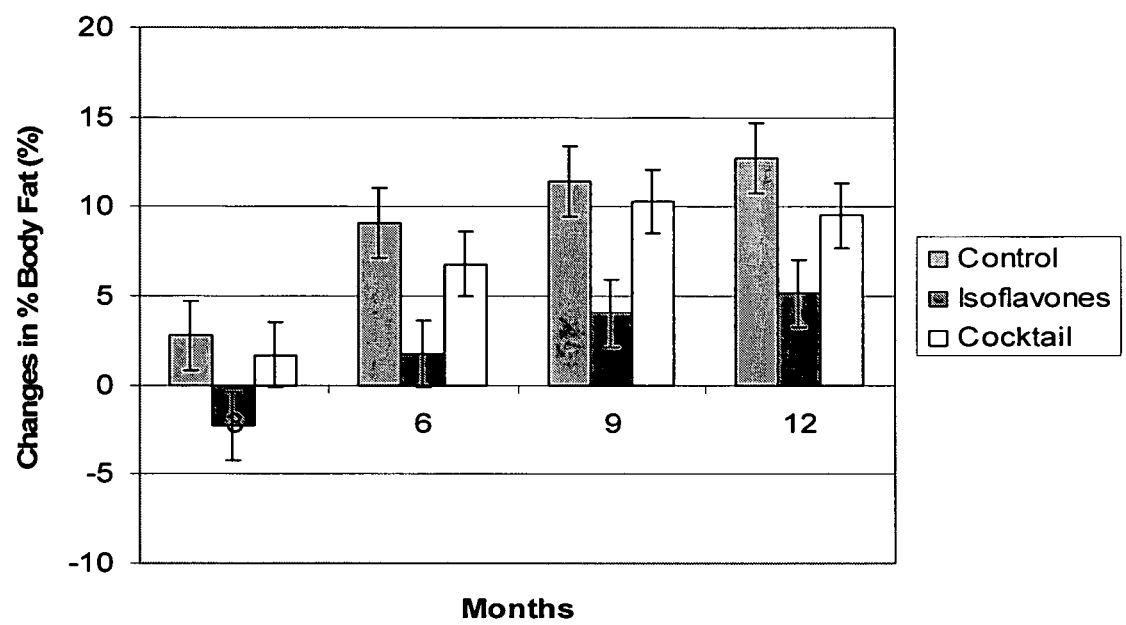
FIG. 4 shows changes in the percentage of body fat over baseline during the 12 month weight management regimen in the dogs fed either the control diet, the isoflavones diet, or the cocktail diet. All dogs were fed excess calories, e.g. 125% of their maintenance energy requirement. Dogs fed the isoflavone diet gained less body fat relative to both the control diet-fed and cocktail diet-fed dogs, as measured at 3, 6, 9, and 12 months ($p<0.05$, between control diet and isoflavone diet groups).

The control group had 5-, 2.8-, and 2.5-fold increase in the percentage of body fat than the isoflavone-fed dogs after 6 (p=0.011, Control vs. Isoflavone group), 9 (p=0.009, Control vs. Isoflavone group) and 12 months (p=0.008, Control vs. Isoflavone group) of feeding, respectively. The cocktail-fed dogs had 3.9-, 2.6-, and 1.9-times more average body fat gain than the isoflavone-fed dogs after 6 (p=0.06, Cocktail vs. Isoflavone group), 9 (p=0.02, Cocktail vs. Isoflavone group) and 12 months (p=0.098, Cocktail vs. Isoflavone group) of feeding, respectively (FIG. 4).

Figure 5:
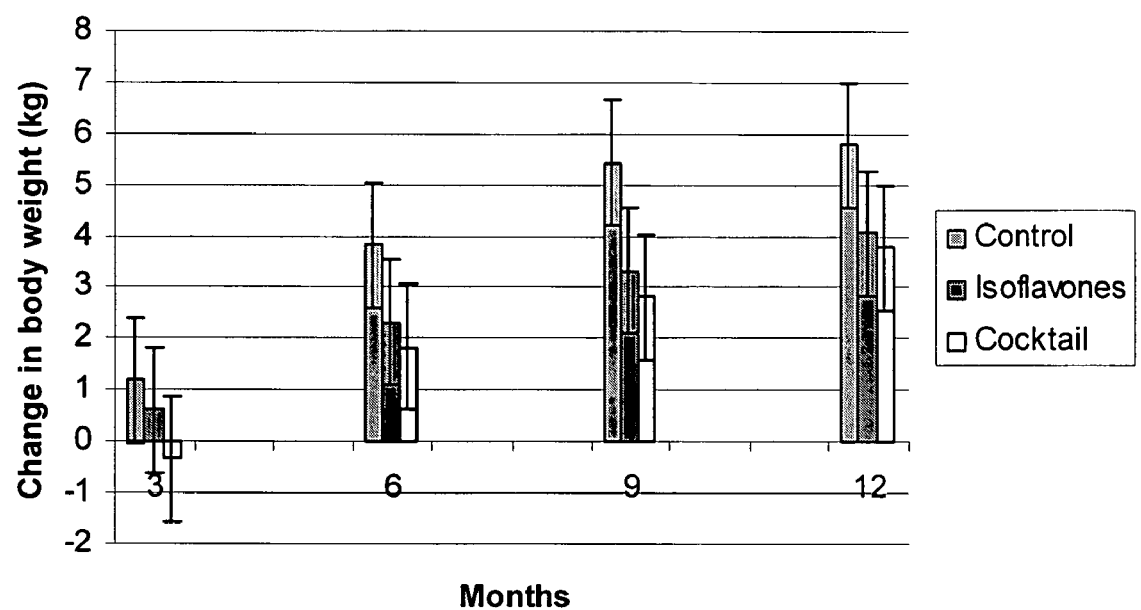
FIG. 5 shows the changes in overall body weight over baseline in spayed female dogs during the 12-month weight management regimen. Spayed female dogs were fed either the control diet, the isoflavone diet, or the cocktail diet. All dogs were fed 125% of their maintenance energy requirement.
Figure 6:
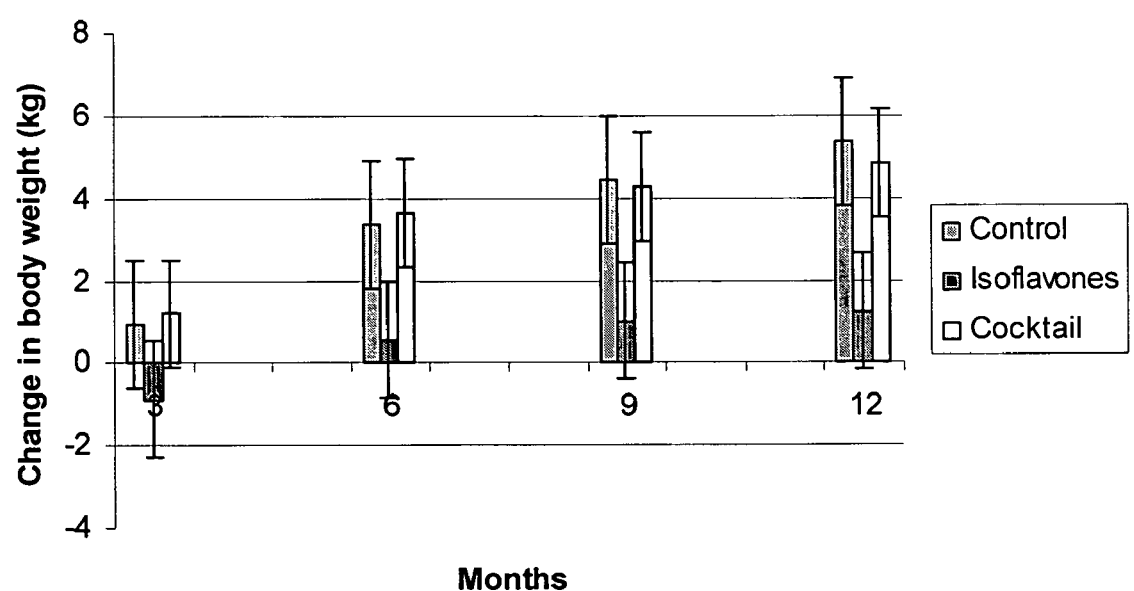
FIG. 6 shows the changes in overall body weight over baseline in neutered male dogs during the 12-month weight management regimen. Neutered male dogs were fed either the control diet, the isoflavone diet, or the cocktail diet. Dogs fed the isoflavone diet gained significantly less overall body weight relative to the dogs fed the control diet, as measured at 3, 6, 9, and 12 months ($p<0.05$). All dogs were fed excess calories, e.g. 125% of their maintenance energy requirement.

Gender-Specific Weight Management Results:

Results are shown in FIGS. 5-10. Weight gain in spayed female dogs was lower in the isoflavone-fed group than in the control group after 6, 9, and 12 months of feeding. Throughout the 12-month study, the average weight gain in the control-fed spayed female dogs was 140% of the weight gain of the isoflavone-fed dogs (FIG. 5). Similarly, weight gain in neutered male dogs was significantly lower in the isoflavone-fed group than in the control group after 6, 9, and 12 months of feeding (the p-value was significant at 12 months). Throughout the 12-month study, the average weight gain in the control-fed neutered male dogs was 428% of that of the isoflavone-fed dogs (FIG. 6).

Figure 7:
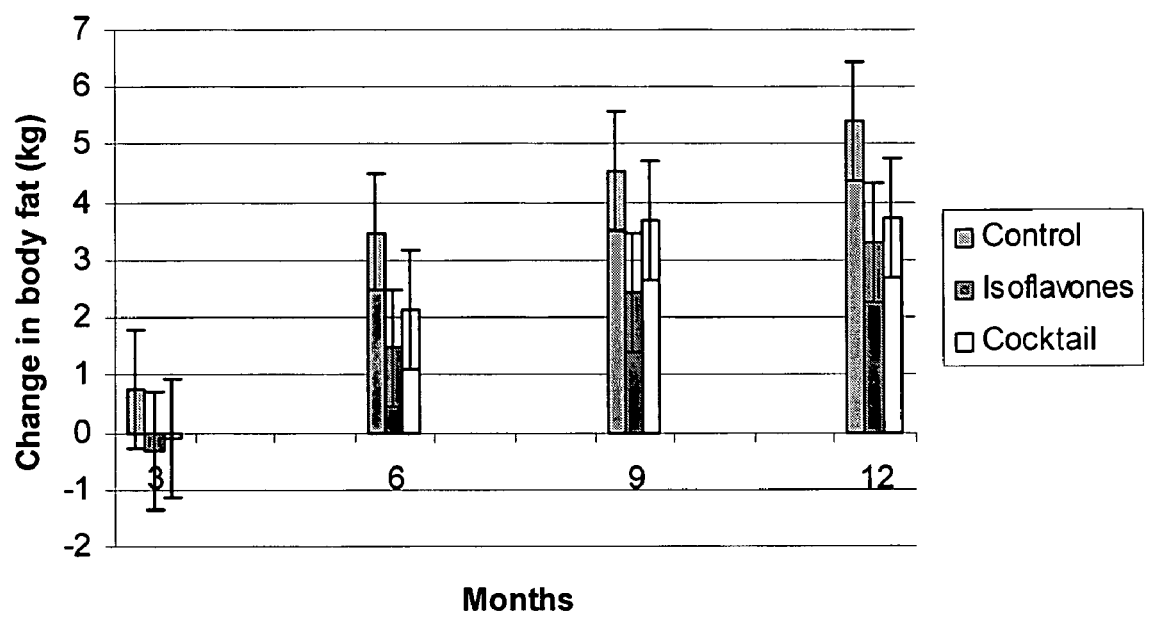
FIG. 7 shows changes in the amount of body fat over baseline in spayed female dogs during the 12 month weight management regimen on either the control diet, the isoflavone diet, or the cocktail diet described above. All dogs were fed 25% more than their maintenance energy requirement.

Changes in the amount of body fat were also monitored for spayed female dogs and neutered male dogs. For both spayed female dogs and neutered male dogs, control- and cocktail-fed groups gained more body fat than the isoflavone group, especially in male dogs. Among spayed female dogs, dogs fed the control diet had 2.4, 1.9, and 1.6-times as much average body fat gain as the isoflavone-fed dogs after 6, 9 and 12 months of feeding, respectively. The cocktail-fed dogs had 1.4, 1.5, and 1.0-times as much average body fat gain as the isoflavone-fed dogs after 6, 9 and 12 months of feeding, respectively (FIG. 7).

Figure 8:
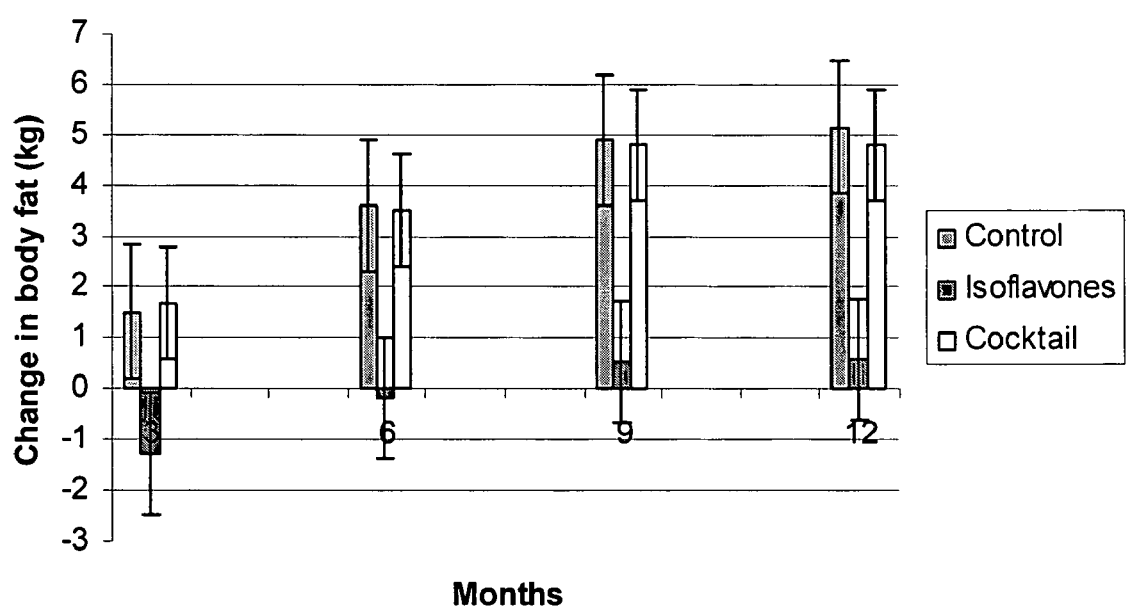
FIG. 8 shows the changes in the amount of body fat over baseline in neutered male dogs during the 12-month weight management regimen on either the control diet, the isoflavone diet, or the cocktail diet as described above. Dogs fed the isoflavone diet gained significantly less overall body weight relative to the dogs fed the control diet or cocktail diet, as measured at 3, 6, 9, and 12 months ($p<0.05$). Here too, the dogs were fed 125% of their maintenance energy requirement.

Among neutered male dogs, dogs fed the control diet had 3.6, 8.9, and 8.7 as much average body fat gain as the isoflavone-fed dogs after 6, 9 and 12 months of feeding, respectively. The cocktail-fed dogs had 3.5, 8.7, and 8.1 times as much average body fat gain as the isoflavone-fed dogs after 6, 9 and 12 months of feeding, respectively (FIG. 8).

Figure 9:
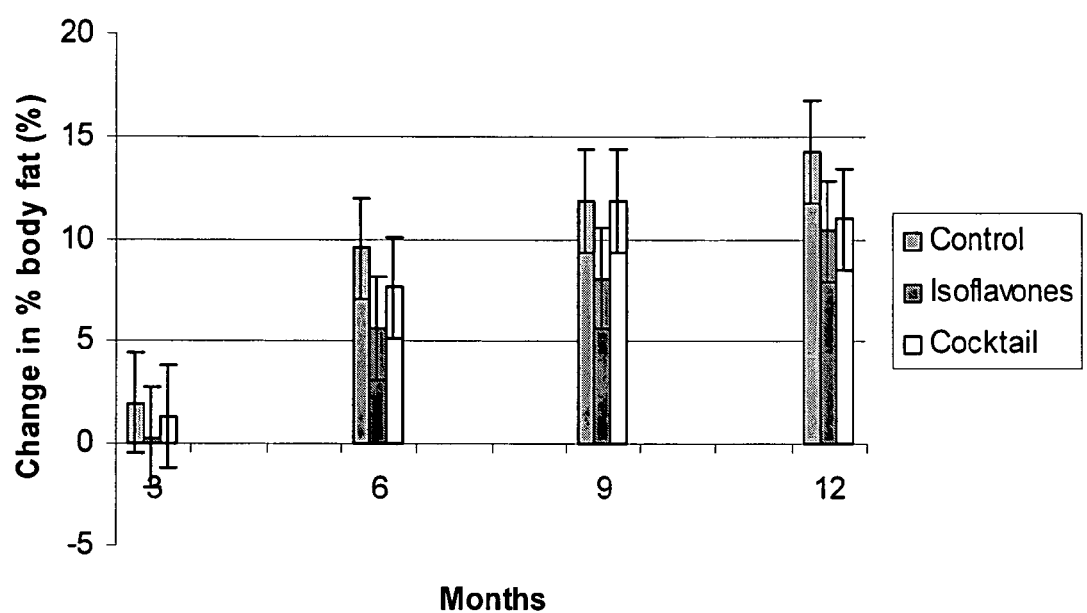
FIG. 9 shows changes in the percentage of body fat over baseline in spayed female dogs during the 12 month weight management regimen on either the control diet, the isoflavone diet, or the cocktail diet described above. The dogs were fed 25% more than their maintenance energy requirement.

With respect to the percentage of body fat, spayed female dogs fed the control diet demonstrated 1.7, 1.5, and 1.4 times the percentage of body fat as the isoflavone-fed dogs after 6, 9 and 12 months of feeding, respectively. Spayed female dogs fed the cocktail diet demonstrated 1.4, 1.5, and 1.1 times the percentage of body fat gain as dogs fed the isoflavones diet after 6, 9 and 12 months of feeding, respectively (FIG. 9).

Figure 10:
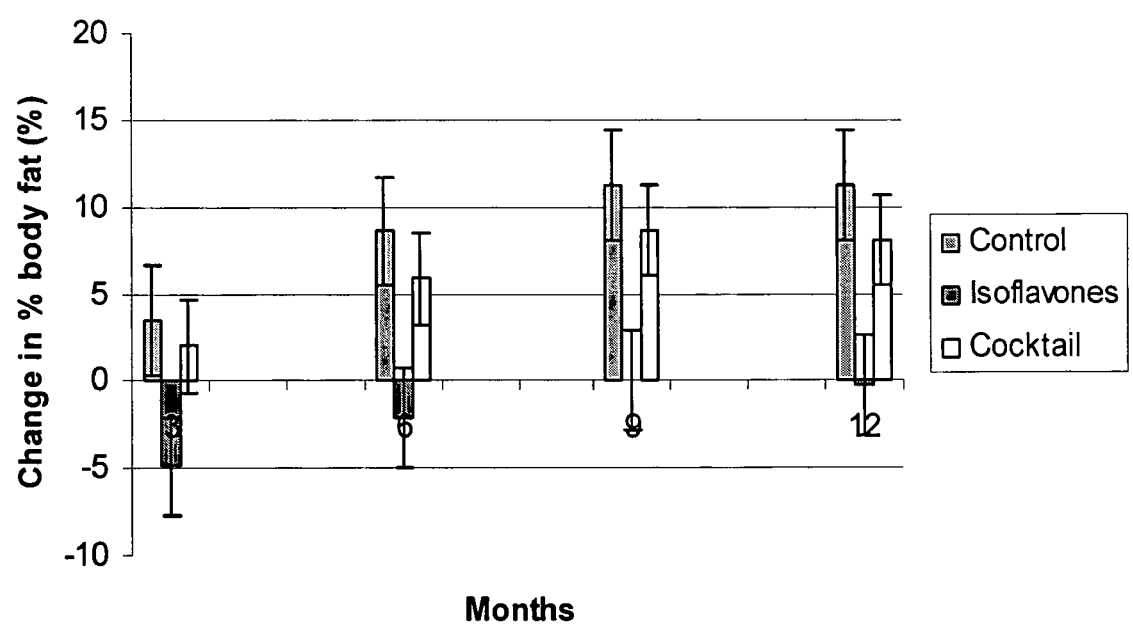
FIG. 10 shows changes in the percentage of body fat over baseline in neutered male dogs during the 12 month weight management regimen receiving either the control diet, the isoflavone diet, or the cocktail diet. Dogs fed the isoflavone diet gained significantly less body fat relative to both the control diet and cocktail diet-fed dogs, as measured at 3, 6, 9, and 12 months ($p<0.05$). All dogs were fed 25% above their maintenance energy requirement.

Neutered male dogs fed the control diet demonstrated 10.7, 11.3, and 11.2 times the percentage of body fat as the isoflavone-fed dogs after 6, 9 and 12 months of feeding, respectively. Neutered male dogs fed the cocktail diet demonstrated 6.0, 8.7, and 8.1 times the percentage of body fat gain as dogs fed the isoflavones diet after 6, 9 and 12 months of feeding, respectively (FIG. 10).

REFERENCES

Bhathena S J, and Velasquez M T (2002) Beneficial role of dietary phytoestrogens in obesity and diabetes. *Am. J. Clin. Nutr.* 76:1191-201.

Chin S F, Liu W, Storkson J M, Ha Y L, and Pariza M W (1992) Dietary sources of conjugated dienoic isomers of linoleic acid, a newly recognized class of anticarcinogens. *J. Food Comp. Anal.* 5:185-97.

Clarkson T B, Anthony, M S, and Morgan T M. (2001) Inhibition of postmenopausal atherosclerosis progression: a comparison of the effects of conjugated equine estrogens and soy phytoestrogens. *J. Clin. Endocrinol. Metab.* 86:41-7.

Cooke P S and Naaz A. (2004) Role of Estrogens in Adipocyte Development and Function. *Exp. Biol. Med.* 229:112735.

Fang Y C, Chen B H, Huang R F, and Lu Y F. (2004) Effect of genistein supplementation on tissue genistein and lipid peroxidation of serum, liver and low-density lipoprotein in hamsters. *J. Nutr. Biochem.* 15:142-8.

Fritz I B, and Yue K T N (1963) Long-chain carnitine acyltransferase and the role of acylcarnitine derivatives in the catalytic increase of fatty acid oxidation induced by carnitine, *J. Lipid Res.* 4:279-88.

Hand M S, Armstrong P J, and Allen T A. (1989) Obesity: Occurrence, treatment, and prevention. *Vet. Clin. North Am. Small Anim. Pract.* 19:447-74.

Harper E J, Stack D M, Watson T D, and Moxham G. (2001) Effects of feeding regimens on bodyweight, composition and condition score in cats following ovariohysterectomy. *J. Small Anim. Pract.* 42:433-8.

Kawakami Y, Tsurugasaki W, Yoshida Y, Igarashi Y, Nakamura S, and Osada K. (2004) Regulative actions of dietary soy isoflavone on biological antioxidative system and lipid metabolism in rats. *J. Agric. Food Chem.* 52:1764-8.

Linford N J, and Dorsa D M. (2002) 17beta-Estradiol and the phytoestrogen genistein attenuate neuronal apoptosis induced by the endoplasmic reticulum calcium-ATPase inhibitor thapsigargin. *Steroids.* 67:1029-40.

Lynch S M, Morrow J D, Roberts II L J, and Frei B. (1994) Formation of non-cyclooxygenasae-derived prostanoids (F2-isoprostanes) in plasma and low density lipoprotein exposed to oxidative stress in vitro. *J. Clin. Invest.* 93:998-1004;

Mohamed, M K and Abdel-Rahman A A. (2000) Effect of long-term ovariectomy and estrogen replacement on the expression of estrogen receptor gene in female rats. *Eur. J. Endocrinol.* 142:307-14.

Morrow J D, Hill K E, Burk R F, Nammour T M, Badr K F, and Roberts II L J. (1990) A series of prostaglandin F2-like compounds are produced in vivo in humans by a non-cyclooxygenase, free radical-catalyzed mechanism. *Proc. Natl. Acad. Sci. USA* 87:9383-7.

Naaz A, Yellayi S, Zakroczymski M A, Bunick D, Doerge D R, Lubahn D B, Helferich W G, and Cooke P S. (2003) The soy isoflavone genistein decreases adipose deposition in mice. *Endocrinology.* 144:3315-20.

Pergola G D. (2000) The adipose tissue metabolism: Role of testosterone and dehydroepiandrosterone. *Int. J. Obesity* 24:S59-S63.

Robertson I D. (2003) The association of exercise, diet and other factors with owner-perceived obesity in privately owned dogs from metropolitan Perth, Wash. *Prev. Vet. Med.* 58:75-83.

Sayegh R A, Kelly L, Wurtman J, Deitch A, and Chelmow D. (1999) Impact of hormone replacement therapy on the body mass and fat compositions of menopausal women: a cross-sectional study. *Menopause.* 6:312-5.

Scarlett J M, Donoghue S, Saidla J, and Wills J. (1994) Overweight cats: prevalence and risk factors. *Int. J. Obes.* 18:S22-8.

Urakawa H, Katsuki A, Sumida Y, Gabazza E C, Murashima S, Morioka K, Maruyama N, Kitagawa N, Tanaka T, Hori Y, Nakatani K, Yano Y, and Adachi Y. (2003) Oxidative stress is associated with adiposity and insulin resistance in men. *J. Clin. Endocrinol. Metab.* 88:4673-6.

Wagner J D, Schwenke D C, Greaves K A, Zhang L, Anthony M S, Blair R M, Shadoan M K, and Williams J K. (2003) Soy protein with isoflavones, but not an isoflavone-rich supplement, improves arterial low-density lipoprotein metabolism and atherogenesis. *Arterioscler. Thromb. Vasc. Biol.* 23:2241-6.

The present invention is not limited to the embodiments described and exemplified above, but is capable of variation and modification within the scope of the appended claims.

What is claimed is:

1. A method for reducing fat accumulation in a male mammal consuming calories in excess of its minimum daily requirement, the method comprising identifying a male mammal, determining that the male mammal is consuming calories in excess of its minimum daily requirement, and providing to the male mammal on a regular basis a comestible composition comprising one or more isoflavones or metabolites thereof in an amount effective for reducing deposition of subcutaneous or intramuscular fat in the body of the male mammal.

2. The method of claim 1 wherein the comestible composition is a pet food, a human food, or a food supplement to be taken directly or added to a human food, pet food, or to animal feed.

3. The method of claim 1 wherein the mammal is a human or a companion animal.

4. The method of claim 3 wherein the companion animal is a dog or a cat.

5. The method of claim 1, further comprising determining that the male mammal is a companion animal that has been neutered; is post-andropausal; has reduced circulating estradiol concentrations relative to a healthy, nonobese male animal of the same species or breed; has reduced ability to convert testosterone into estradiol relative to a healthy, nonobese male animal of the same species or breed; or has reduced aromatase activity relative to a healthy, nonobese male animal of the same species or breed.

6. The method of claim 1, wherein the composition has a sparing effect on lean body mass.

7. The method of claim 5, further comprising the step of determining that the companion animal has been neutered after weaning but before reaching sexual maturity, and wherein the comestible composition is provided to the companion animal before the animal reaches a normal adult body weight.

8. The method of claim 1, wherein the composition is provided by administering to the male mammal on a daily basis.

9. The method of claim 1, further comprising determining that the male mammal is a companion animal that has not been neutered and is not post-andropausal.

10. The method of claim 1, further comprising the step of determining that the male mammal is beyond the mid-point of the life expectancy for its species or breed.

11. The method of claim 7, wherein the companion animal is a neutered puppy or kitten.

12. The method of claim 5, further comprising the step of determining that the circulating estradiol of the animal is less than about 80% of a healthy, nonobese male animal of the same species or breed.

13. The method of claim 5, further comprising the step of determining that the circulating estradiol of the animal is less than about 50% of a healthy, nonobese male animal of the same species or breed.

14. The method of claim 5, further comprising the step of determining that the circulating estradiol of the animal is less than about 20% of a healthy, nonobese male animal of the same species or breed.

15. The method of claim 5, further comprising the step of determining that the circulating estradiol of the animal is less than about 10% of a healthy, nonobese animal of the same species or breed.

* * * * *

UNITED STATES PATENT AND TRADEMARK OFFICE
CERTIFICATE OF CORRECTION

PATENT NO. : 8,226,973 B2
APPLICATION NO. : 11/592471
DATED : July 24, 2012
INVENTOR(S) : Yuanlong Pan It is certified that error appears in the above-identified patent and that said Letters Patent is hereby corrected as shown below:

In the Claims

Col. 18, lines 1-10

Claim 1, which currently reads: "A method for reducing fat accumulation in a male mammal consuming calories in excess of its minimum daily requirement, the method comprising identifying a male mammal, determining that the male mammal is consuming calories in excess of its minimum daily requirement, and providing to the male mammal on a regular basis a comestible composition comprising one or more isoflavones or metabolites thereof in an amount effective for reducing deposition of subcutaneous or intramuscular fat in the body of the male mammal" should read --A method for reducing fat accumulation in a male mammal consuming calories in excess of its minimum daily requirement, the method comprising identifying a male mammal, determining that the male mammal is consuming calories in excess of its minimum daily requirement, and providing to the male mammal on a regular basis a comestible composition comprising equol in an amount effective for reducing deposition of subcutaneous or intramuscular fat in the body of the male mammal--.

Signed and Sealed this
Eighth Day of July, 2014

Michelle K. Lee
*Deputy Director of the United States Patent and Trademark Office*